United States Patent [19]

Schmolka

[11] Patent Number: 4,544,495

[45] Date of Patent: * Oct. 1, 1985

[54] HIGH FOAMING LIQUID SHAMPOO COMPOSITION

[75] Inventor: Irving R. Schmolka, Grosse Ile, Mich.

[73] Assignee: BASF Wyandotte Corporation, Wyandotte, Mich.

[*] Notice: The portion of the term of this patent subsequent to Apr. 27, 1999 has been disclaimed.

[21] Appl. No.: 291,265

[22] Filed: Aug. 10, 1981

[51] Int. Cl.$^4$ ................................................ C11D 1/722
[52] U.S. Cl. ............................ 252/174.21; 252/173; 252/174.22; 252/DIG. 1; 252/DIG. 13; 252/DIG. 14
[58] Field of Search ............ 252/174.21, 174.22, 252/173, DIG. 1, DIG. 13, DIG.14; 424/70; 568/624

[56] References Cited

U.S. PATENT DOCUMENTS

| | | | |
|---|---|---|---|
| Re. 29,909 | 2/1979 | Kurtz | 252/106 |
| 2,828,345 | 3/1958 | Spriggs | 568/624 |
| 3,101,374 | 8/1963 | Patton | 252/174.21 |
| 3,337,463 | 8/1967 | Schmolka | 252/89 |
| 3,869,399 | 3/1975 | Collins | 252/559 |
| 3,925,241 | 12/1975 | Schmolka | 252/DIG. 13 |
| 4,220,548 | 7/1980 | Hashimoto | 252/106 |
| 4,326,977 | 4/1982 | Schmolka | 252/106 |

FOREIGN PATENT DOCUMENTS

| | | |
|---|---|---|
| 55-12210 | 9/1980 | Japan . |
| 0722746 | 1/1955 | United Kingdom . |
| 1563808 | 4/1980 | United Kingdom . |

OTHER PUBLICATIONS

Cosmetic Formulary, BASF Wyandotte Corporation, Industrial Chemicals Group, Wyandotte, Michigan 48192.

Primary Examiner—Paul Lieberman
Assistant Examiner—Hoa Van Le
Attorney, Agent, or Firm—Bernhard R. Swick

[57] ABSTRACT

A shampoo composition containing a polyoxybutylene-polyoxyethylene nonionic surfactant has unexpectedly high viscosity and high foam.

3 Claims, No Drawings

HIGH FOAMING LIQUID SHAMPOO COMPOSITION

BACKGROUND OF THE INVENTION

1. Field of the Invention

The invention relates to a shampoo composition containing a cogeneric mixture of conjugated polyoxybutylene-polyoxyethylene compounds as a nonionic surfactant. The nonionic surfactant is non-irritating to the eyes, and formulations of the shampoos have unexpectedly high viscosity and high foam.

2. Description of the Prior Art

U.S. Pat. No. 3,337,463 relates to nonionic detergent compositions having enhanced and stabilized foaming characteristics. The foaming detergent compositions consist essentially of a mixture of polyoxylkylene condensates of cellulose and at least one nonionic surfactant such as a mixture of conjugated polyoxyethylene-polyoxypropylene componds of the formula $$HO(C_2H_4O)_a(C_3H_6O)_b(C_2H_4O)_cH$$

wherein b is an integer sufficiently high to provide a molecular weight of at least about 900 for the oxypropylene base and wherein a+c is an integer sufficiently high to provide 5 to 90 percent of the total molecular weight of the compound. The BASF Wyandotte "Cosmetic Formulary" includes therein various shampoo compositions using nonionic surfactants conforming to the above formula.

Some of the problems of the prior art shampoo compositions have been irritation of the eyes, low foaming and low viscosity, causing a thin watery, consistency. The present invention is directed to the preparation of a shampoo composition without these problems.

SUMMARY OF THE INVENTION

The invention relates to a shampoo comprising from 2 to 25 percent by weight of a nonionic surfactant and from 75 to 98 percent by weight water. The nonionic surfactant is a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom, thereby principally constituting a polyoxybutylene polymer. The oxyethylene groups are attached to the polyoxybutylene polymer in polyoxyethylene chains. The average molecular weight of the polyoxybutylene polymers in the mixture is at least 500, as determined by hydroxyl number, and the oxyethylene groups present constitute 65 to 80 percent by weight of the compound. In a preferred embodiment 1 to 35 percent by weight of additives and 0 to 50 percent by weight of other surfactants are added.

DESCRIPTION OF THE PREFERRED EMBODIMENTS

The nonionic surfactant of use in the invention is a cogeneric mixture of conjugated polyoxybutylene polyoxyethylene compounds having as a hydrophobe, a polyoxybutylene polymer of at least 500 molecular weight. The polyoxybutylene compounds are prepared by first condensing butylene oxide with an organic compound containing a plurality of reactive hydrogen atoms to prepare a polyoxybutylene polymer of at least 500 molecular weight, and subsequently condensing ethylene oxide thereto. The compounds used in this invention conform to the following generic formula:

$$Y[(C_4H_8O)_n\text{—E—H}]_x \quad (A)$$

wherein Y is the residue of a water soluble organic compound containing therein x active hydrogen atoms; n is an integer; x is an integer greater than 1; the values of n and x are such that the molecular weight of the compound, exclusive of E, is at least 500, as determined by hydroxyl number; E is a polyoxyalkylene chain wherein the oxygen/carbon atom ratio is at least 0.5, and E constitutes 65 percent by weight to 80 percent by weight of the compound.

The polyoxybutylene polymer, which is an intermediate in the preparation of the compounds of use in this invention, has the following structure:

$$Y[(C_4H_8O)_nH]_x \quad (B)$$

wherein Y, n and x are defined as in Formula A above.

The preferred compounds of use in this invention are prepared by condensing ethylene oxide in an amount between 65 and 80 percent by weight of the resultant compound, with the polyoxybutylene polymer. These compounds have the following formula $$Y[(C_4H_8O)_n(C_2H_4O)_mH]_x \quad (C)$$

wherein Y, n and x are defined as in Formula A and m has a value such that the oxyethylene groups constitute 65 to 80 percent by weight of the compound.

When ethylene oxide is condensed with a polyoxybutylene glycol of at least 500 molecular weight and derived from a butanediol initiator, the resulting compounds have the following structure:

$$HO(C_2H_4O)_m(C_4H_8O)_n(C_2H_4O)_{m'}H \quad (D)$$

where n is defined as previously set forth; and m'+m have a value such that the oxyethylene groups constitute 65 percent by weight to 80 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators which may include water, diols such as propane diol, butanediol, triols such as glycerol and trimethylol propane, tetrols such as pentaerythritol as well as initiators containing more than four hydroxyl groups such as hexitol or sucrose. Also, amines and other low molecular weight water-soluble compounds having two or more active hydrogen atoms, such as ethylene diamine or diethylene triamine, may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the surfactants used in this invention. In lieu of butylene oxide, other 4-carbon cyclic ethers such as methyloxetane, tetrahydrofuran and isobutylene oxide may be used.

Surfactants of the invention, conforming to structure D above, are those surfactants which contain a hydrophobe of between about 600 and about 1800 molecular weight and an ethylene oxide content of from about 65 to 80 percent by weight of the surfactant. Preferably used is a surfactant having a hydrophobe of about 1200 molecular weight and containing about 70 percent by weight ethylene oxide. The surfactant is used in an amount between 2 and 25 percent by weight of the shampoo.

The nonionic surfactant used in the shampoo compositions of this invention may be supplemented by the addition of other surfactants, i.e., amphoteric, anionic or cationic, and nonionic surfactants. Examples of amphoteric surfactants useful in the invention are generally water soluble salts of derivatives of aliphatic amines which contain at least one cationic group, ergo, non-quaternary nitrogen, quaternary ammonium, or quaternary phosphonium group, at least one alkyl group of about 8 to 18 carbon atoms and an anionic water solubilizing carboxyl, sulfo, sulfato, phosphato or phosphono group in their molecular structure. Cocoamidopropyl betaine is useful. The alkyl group may be straight chain or branched and the specific cationic atom may be part of a heterocyclic ring. Specific examples are disclosed in U.S. Pat. No. 3,849,548, U.S. Pat. No. 3,959,462, and U.S. Pat. No. 4,061,602. Suitable anionic surfactants include those surface-active agents which contain an organic hydrophobic group containing generally 8 to 26 carbon atoms, preferably 10 to 18 carbon atoms in their molecular structure, and at least one water solubilizing group selected from the group of sulfonate, sulfate, carboxylate, phosphonate and phosphate so as to form a water-soluble detergent. Specific examples of suitable anionic surfactants are disclosed in U.S. Pat. No. 3,849,548, U.S. Pat. No. 4,126,674, U.S. Pat. No. 4,061,602, and U.S. Pat. No. 3,928,251. Useful cationic surfactants are those disclosed in U.S. Pat. Nos. 3,849,548, 3,959,462 and 4,126,624. Other nonionic surfactants such as ethoxylated sorbitan esters, alkanolamides and fatty acid esters may be used as well as those mentioned in U.S. Pat. Nos. 3,849,548, 3,959,462 and 4,126,674. The other surfactants are added in an amount between 0 to 50 percent by weight. The anionic surfactants may be added in an amount between 0.5 and 30, preferably 2 to 10 percent by weight. The amphoteric surfactants may be added between 2 and 40, preferably 5 to 30 percent by weight. The cationic surfactants may be used in an amount between 0.2 and 5.0 percent by weight and the other nonionics may be used in an amount between 0.5 and 10 percent by weight.

The shampoo compositions of certain embodiments of this invention also include additives such as thickening agents, fatty acid esters such as polyoxyethylene glycol 6000 distearate (PEG 6000 distearate); foam boosting and foam stabilizing agents, such as alkanolamides and amine oxides such as lauric diethanolamide (lauramide DEA), lauryl dimethyl amine oxide and lauric isopropanolamide; and those additives such as disclosed in U.S. Pat. No. 3,769,398, such as 1-hydroxyethyl-2-Cocoimidazoline and 2-Coco 4,4-dihydroxy methyloxazoline. Other suitable additives for the shampoo compositions of this invention include calcium and magnesium ion-chelating agents, such as ethylenediaminetetra-acetic acid (EDTA) and other sequestering agents; inorganic or organic acids, such as phosphoric and citric acid; or alkalis, to adjust pH; preservatives such as methyl p-hydroxybenzoate and other anti-mirobial agents, perfume, lanolin and its derivatives or other emollients, conditioning agents, water and anti-dandruff agents, dyes, fragrances, alcohol, glycol, other thickening agents such as cellulose derivatives, gums, alkoxylated fatty acids and opacifiers. The additives are added in an amount between 1 and 35, preferably 5 and 15 percent by weight of the shampoo. Each additive, if included, is used in an amount between 0.01 and 8.0 percent by weight. It is understood that not all of the within-mentioned additives will be used in each shampoo formulation. The expert in shampoo formulation is able to adjust the type and quantity of additives necessary to arrive at a suitable shampoo formulation.

The shampoos of the invention are prepared as follows: water is added to a vessel equipped with a mechanical stirrer. The other ingredients are added slowly, individually or as a group, and mixed until dissolved. Some heat may be used to hasten solution. The fragrance and preservative are added last after a homogeneous solution is formed.

The following surfactants A and B, made from a polyoxybutylene hydroprobe prepared from condensing 1,2-butylene oxide with a 1,4-butanediol initiator, and comparisons M and N are used in the examples:

Surfactant A is a polyoxybutylene-polyoxyethylene nonionic surfactant of this invention having an approximate average molecular weight of the polyoxybutylene hydrophobe of about 1200 and a polyoxyethylene hydrophile content of about 70 percent by weight of the surfactant.

Surfactant B is a polyoxybutylene-polyoxyethylene nonionic surfactant of this invention having an approximate average molecular weight of the polyoxybutylene hydrophobe of about 1200 and a polyoxyethylene hydrophile content of about 80 percent by weight of the surfactant.

Comparison M is a polyoxypropylene-polyoxyethylene nonionic surfactant having a molecular weight of a polyoxypropylene hydrophobe of about 2250 and a polyoxyethylene hydrophile content of about 70 percent by weight of the surfactant.

Comparison N is a commercial shampoo recently introduced on the market called AGREE.

The following examples will further illustrate the various aspects of the invention where not otherwise specified throughout this specification and claims, temperatures are in degrees Centigrade, and parts, percentages and proportions are by weight.

EXAMPLES 1–3

Examples 1–3, examples of shampoo formulations of the invention, are prepared according to the preceding description of preparation.

EXAMPLE 1

| Component | Parts by Weight |
|---|---|
| Surfactant A | 24 |
| PEG 6000 Distearate | 2 |
| Lanolin | 4 |
| Perfume | 0.5 |
| Preservative | 0.2 |
| Water | 67.3 |
| Lauric dimethylamine oxide | 2.0 |

EXAMPLE 2

| Surfactant A | 18 |
|---|---|
| Cocamidopropyl betaine (30% active) | 6 |
| Lauric diethanolamide | 2 |
| Sodium carboxymethyl cellulose | 2 |
| Acetic acid (to pH 6) | q.s. |
| Perfume | 0.4 |
| Preservative | 0.2 |
| Opacifier | 0.5 |
| Sequestering agent (ethylenediaminetetraacetic acid) | 0.2 |
| Water | 70.7 |

EXAMPLE 3

| Surfactant A | 20 |
|---|---|
| Sodium lauryl ether sulfate (58% active) | 5 |
| Zinc Pyrithione | 0.5 |
| Ethylenediaminetetraacetic acid | 0.5 |
| Methyl cellulose | 0.7 |
| Coconut fatty acids monoethanolamide | 3 |
| Perfume | 0.5 |
| Citric Acid (to pH 5) | q.s. |
| Ethoxylated lanolin | 2 |
| Water | 67.8 |

EXAMPLES 4 THROUGH 7 AND COMPARISON EXAMPLES M AND N

Shampoo formulations 4 through 7 and Comparison M were prepared according to the general procedure for Examples 1-3.

EXAMPLE 4

| Surfactant B | 11.6 |
|---|---|
| Cocamidopropyl betaine (30% active) | 8.4 |
| PEG 6000 distearate | 2.0 |
| Citric Acid | 0.1 |
| Water | 74.9 |
| Lauramide DEA | 3.0 |

EXAMPLE 5

| Surfactant B | 11.6 |
|---|---|
| Tetrahydroxy propyl ethylene diamine lauryl ether sulfate (53.5% active) | 3.8 |
| 99.8% Citric Acid | 0.1 |
| Lauric diethanolamide | 3.0 |
| Cocamidopropyl betaine (30% active) | 21.3 |
| PEG 6000 Distearate | 2.0 |
| Distilled Water | 58.1 |

EXAMPLE 6

| Surfactant B | 11.6 |
|---|---|
| 99.8 Citric Acid | 0.1 |
| Lauric diethanolamide | 3.0 |
| Cocamidopropyl betaine (30% active) | 28.0 |
| PEG 6000 Distearate | 2.0 |
| Distilled Water | 55.2 |

EXAMPLE 7

| Surfactant A | 11.6 |
|---|---|
| 99.8% Citric Acid | 0.1 |
| Lauric diethanolamide | 3.0 |
| Cocamidopropyl betaine (30% active) | 28.0 |
| PEG 6000 Distearate | 2.0 |
| Distilled Water | 55.2 |

COMPARISON M

| Comparison M | 11.6 |
|---|---|
| 99.8% Citric Acid | 0.1 |
| Lauric diethanolamide | 3.0 |
| Cocamidopropyl betaine (30% active) | 28.0 |
| PEG 6000 Distearate | 2.6 |
| Distilled Water | 55.2 |

Bacon foam height tests were conducted to exhibit the high foaming shampoo compositions of applicant's invention. The foam heights of a 15 percent solution, as is, are shown in Table I and the foam heights of a 15 percent solution with 1 percent synthetic sebum soil are shown in Table II.

TABLE I

| Sample | Initial | 2 Min. | 5 Min |
|---|---|---|---|
| Example 5 | 650 mls | 630 mls | 630 mls |
| Example 6 | 730 mls | 720 mls | 720 mls |
| Example 7 | 800 mls | 750 mls | 750 mls |
| Comparison M | 650 mls | 640 mls | 630 mls |
| Comparison N | 240 mls | 140 mls | 100 mls |

TABLE II

| Sample | Initial | 2 Min | 5 Min. |
|---|---|---|---|
| Example 5 | 200 mls | 200 mls | 190 mls |
| Example 6 | 190 mls | 180 mls | 180 mls |
| Example 7 | 120 mls | 120 mls | 120 mls |
| Comparison M | no foam | no foam | no foam |
| Comparison N | no foam | no foam | no foam |

In order to show the surprisingly high viscosity values of a shampoo of this invention, when compared with a shampoo containing the closest structured surfactants of the prior art (M), viscosity tests were run on the shampoos of Examples 4-7 and Comparison M. These values are shown in Table III below.

TABLE III

| Example | Viscosity in cps at 25° C. |
|---|---|
| 4 | 950 |
| 5 | 6393 |
| 6 | 2487 |
| 7 | 390 |
| M | 187 |

The examples show (1) the advantage of the shampoo compositions of the invention over Comparison M in foam and in viscosity and (2) the advantage of the compositions of the application when compared with Comparison N in foam under conditions of soil load and no-soil load.

The embodiments of the invention in which an exclusive privilege or property is claimed are defined as follows:

1. A high foaming liquid shampoo comprising 2 to 25 percent by weight of a nonionic surfactant, 0.01 to 8 percent by weight of an acid suitable for use in shampoos, 0.01 to 8 percent by weight of a foam boosting and foam stabilizing agent, 2 to 40 percent by weight of an amphoteric surfactant, 0.01 to 8 percent by weight of an additional thickening agent and 30 to 80 percent by weight of water, the nonionic surfactant being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains, the average molecular weight of the polyoxybutylene polymers in the mixture being at least 500, as determined by hydroxyl number, and the oxyethylene groups present constituting 65 to 80 percent, by weight, of the mixture.

2. The shampoo of claim 1 wherein the polyoxybutylene polymer molecular weight is about 1200 and the oxyethylene groups present constitute about 70 percent by weight of the mixture.

3. The shampoo of claim 1 wherein the polyoxybutylene polymer molecular weight is about 1200 and the oxybutylene groups present constitute about 80 percent by weight of the mixture.

* * * * *